(12) United States Patent
Li

(10) Patent No.: US 7,500,992 B2
(45) Date of Patent: Mar. 10, 2009

(54) DISTRACTABLE BODY AUGMENTER CAPABLE OF BEING PLANTED THROUGH A PEDICLE FOR VERTEBRAL BODY RECONSTRUCTION

(76) Inventor: Kung-Chia Li, 2Fl-2, No. 335, Sec. 2, Shpai Rd., Beitou Chiu, Taipei (TW)

( * ) Notice: Subject to any disclaimer, the term of this patent is extended or adjusted under 35 U.S.C. 154(b) by 907 days.

(21) Appl. No.: 10/957,717

(22) Filed: Oct. 5, 2004

(65) Prior Publication Data

US 2006/0085007 A1    Apr. 20, 2006

(51) Int. Cl.
  *A61F 2/44* (2006.01)
(52) U.S. Cl. ..................................... 623/17.11
(58) Field of Classification Search ... 623/17.11–17.16; 606/61, 90, 246–249, 279, 105, 282
  See application file for complete search history.

(56) References Cited

U.S. PATENT DOCUMENTS

| | | | | |
|---|---|---|---|---|
| 5,888,228 A | * | 3/1999 | Knothe et al. ............ | 623/17.16 |
| 6,176,882 B1 | * | 1/2001 | Biedermann et al. ..... | 623/17.15 |
| 6,454,807 B1 | * | 9/2002 | Jackson .................... | 623/17.15 |
| 6,685,742 B1 | * | 2/2004 | Jackson .................... | 623/17.11 |
| 2005/0203625 A1 | * | 9/2005 | Boehm et al. ............ | 623/17.11 |

\* cited by examiner

*Primary Examiner*—Eduardo C Robert
*Assistant Examiner*—David Comstock
(74) *Attorney, Agent, or Firm*—Rosenberg, Klein & Lee

(57) ABSTRACT

A distractable body augmenter is provided for reconstruction of a vertebra subjected to loss of bone mass or fracture, and is planted in the vertebra from a pedicle of the vertebra for helping maintain or restore normal position and size of the vertebra; through the pedicle, the augmenter, fitting the pedicle anatomy, was created to reconstruct the fractured or collapsed vertebral body; the augmenter includes a lower planted block, an upper planted block fitted to the lower block in a longitudinally displaceable manner, and a wedge-shaped bar, which is inserted between the upper and the lower blocks for changing the height of the augmenter after the upper and the lower blocks have been planted in a vertebra via a planting tunnel on a pedicle of the vertebra; the fractured body was reduced and maintained by the augmenter until the bone growth and fracture union.

8 Claims, 7 Drawing Sheets

DISTRACTABLE BODY AUGMENTER CAPABLE OF BEING PLANTED THROUGH A PEDICLE FOR VERTEBRAL BODY RECONSTRUCTION

BACKGROUND OF THE INVENTION

1. Field of the Invention

The present invention relates to a distractable body augmenter capable of being planted through a pedicle for vertebral body reconstruction, more particularly, which is used for treatment of vertebral burst fractures, and vertebral compression fractures.

2. Brief Description of the Prior Art

Vertebral body fractures including acute burst fracture or chronic compression fracture with kyphosis were treated in various ways. Acute burst fracture can be treated conservatively, surgical posterior instrumentation, or even anterior bone graft and posterior instrumentation. However, conservative treatment is limited to those with neural intact, non-osteoporosis, good compliance to wear brace and less kyphosis. Posterior instrumentation alone is easy and simple but may lead to 20% implant failure. However, combining anterior and posterior approaches proved to have mechanical advantages, but surgery itself is a suffering to elder patients. The best way to those not good for conservative treatment will be posterior approach with functions of anterior approach simultaneously.

In chronic osteoporotic compression fractures may induce lots of morbilities including chronic back pain, GI dysfunction, decreased pulmonary vital capacity, and feasible new compression fractures. The various methods including surgical instrumentation, vertebral augmentation with cement, kyphoplasty etc. The techniques improved and results become better recently. However, instrumentation may induce decreased spine ROM, implant failure, and adjacent segment disease. The cement either in augmentation or kyphoplasty may induce cement disease. The kyphosis correction is not perfect in kyphoplasty especially the chronic cases with anterior partial or fully fusion. The body augmenter tried to correct the collapsed vertebral body and lead to union with bone graft either combined short posterior instrumentation or cement techniques.

SUMMARY OF THE INVENTION

It is a main object of the present invention to provide a distractable body augmenter, which can be planted into an osteoporosis-effected vertebra from a pedicle of the vertebra, for helping maintain or restore normal position and size of the vertebra.

Through the vertebral pedicle, a device, fit the pedicle anatomy, was created to reconstruct the fractured or collapsed vertebral body. Through the pedicle, the augmenter, fitting the pedicle anatomy, was created to reconstruct the fractured or collapsed vertebral body. The augmenter includes a lower block, an upper block fitted in, and longitudinally displaceable relative to the lower block, and a wedge-shaped bar, which is inserted between the upper and the lower blocks for changing the height of the augmenter after the upper and the lower blocks have been planted in a vertebra via a planting tunnel on a pedicle of the vertebra. After the distractable body augmenter is planted in a vertebra, harvested autogenous bone or artificial bone is injected into the vertebra such that the space in the vertebra are filled with the injected bone, and the body augmenter is securely fixed in positiion. The fractured body was reduced and maintained by the augmenter until the bone growth and fracture union.

BRIEF DESCRIPTION OF THE DRAWINGS

The present invention will be better understood by referring to the accompanying drawings, wherein.

DETAILED DESCRIPTION OF THE PREFERRED EMBODIMENTS

Figure 1:
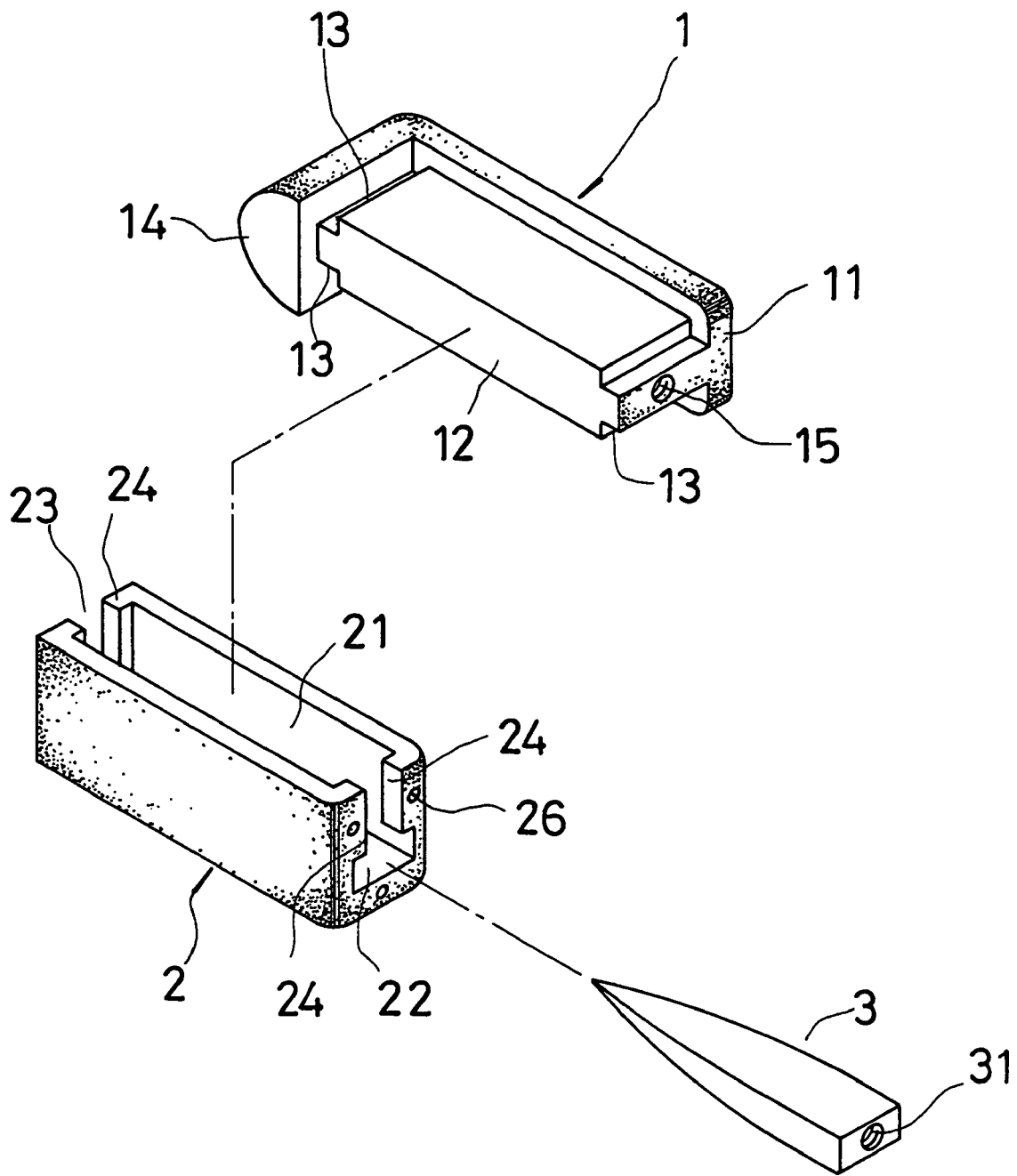
FIG. 1 is an exploded perspective view of the first embodiment of a distractable body augmenter for vertebral body reconstruction.

Referring to FIG. 1, a first embodiment of a distractable body augmenter for vertebral body reconstruction in the present invention includes an upper planted block 1, a lower planted block 2, and a wedge-shaped bar 3.

Both the upper and the lower planted blocks 1 and 2 have rough surfaces with small bumps all over. The upper planted block 1 has an uppermost portion 11, an insertion portion 12 projecting down from a lower side of the uppermost portion 11, and a base 14 joined to a rear end of the insertion portion 12. The insertion portion 12 has longitudinal fitting trenches 13 on two sides of front end and rear end thereof, and a screw hole 15 on the front end. The base 14 has a convexly curved outer side.

The lower planted block 2 has two lengthways extending lateral portions 24, a holding cavity 21 between the lateral portions 24, an inverted T-shaped gap 22 at a front end thereof, and an U-shaped gap 23 at a rear end; the gaps 22 and 23 communicate with the holding cavity 21, and oppose each other.

The wedge-shaped bar 3 has a screw hole 31 on a front end thereof, to which a tool can be connected to help planting.

Figure 2:
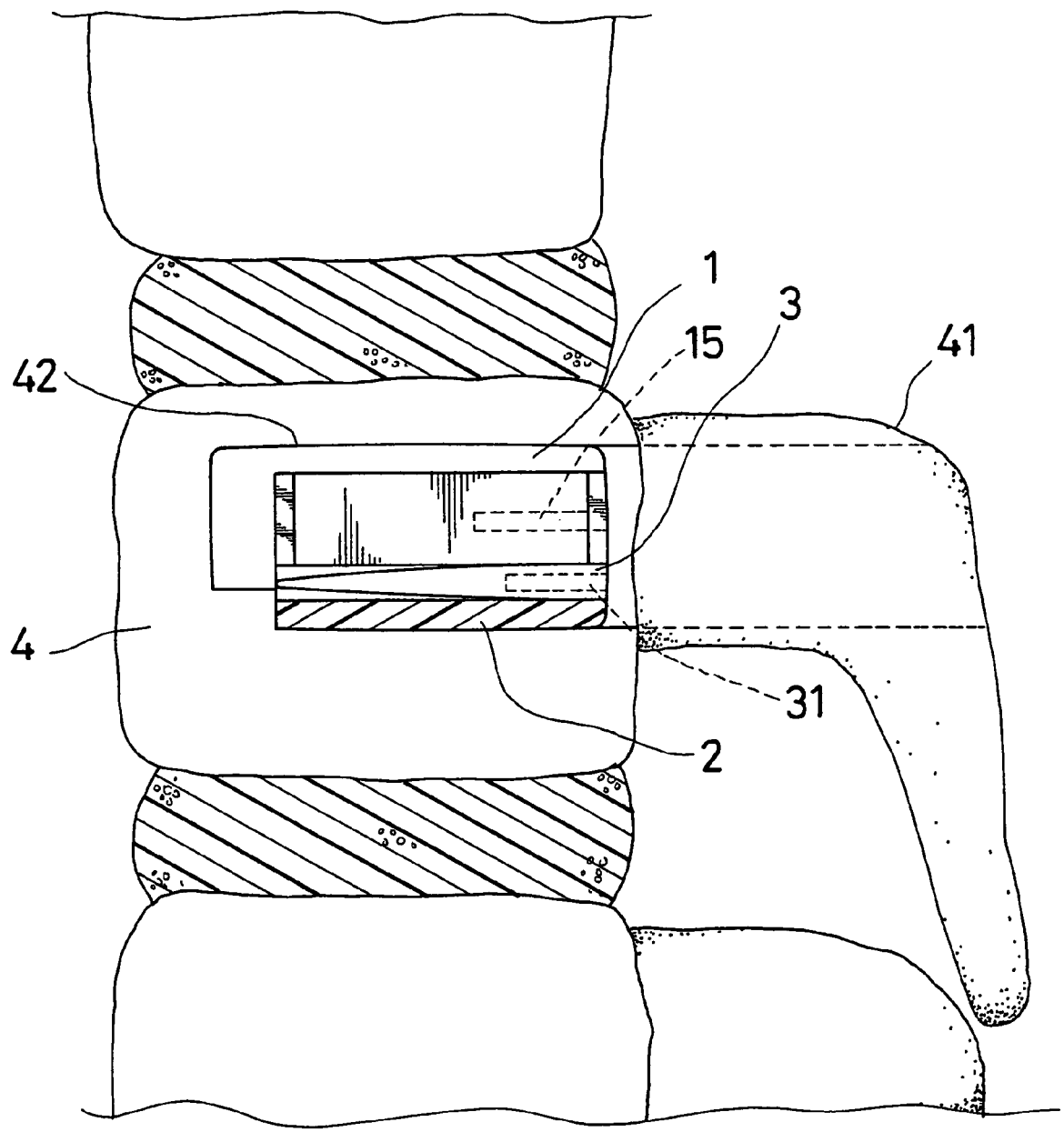
FIG. 2 is a view of the first embodiment of a distractable body augmenter for vertebral body reconstruction, planted in a vertebra.

Referring to FIG. 2, to plant the distractable body augmenter into a vertebra 4, first a planting hole 42 is formed on a pedicle 41 of the vertebra 4. Second, a planting tool (not shown) is screwed into the screw hole 15 of the upper planted block 1, and the upper planted block 1 is inserted in the holding cavity 21 of the lower planted block 2 at the insertion portion 12 thereof with the front and the rear ends, which have the fitting trenches 13 on two sides, being fitted in the gaps 22 and 23 of the lower planted block 2. Then, the upper and the lower planted blocks 1 and 2 together are planted in the vertebra 4 through the planting hole 42 with the help of the planting tool, and the planting tool is removed from the upper planted block 1, and the wedge-shaped bar 3 is inserted in between the insertion portion 12 and a bottom of the lower planted block 2 with the help of another tool (not shown), which is screwed in the screw hole 31; thus, the height of the present augmenter increases, and the vertebra 4 is enlarged in longitudinal direction. Finally, harvested autogenous bone or artificial bone is injected into the vertebra 4 through the planting hole 41 such that both the hollow area of the distractable body augmenter and the space between the distractable body augmenter and the vertebra 4 are filled with the injected bone, and the distractable body augmenter is secured in position.

Figure 3:
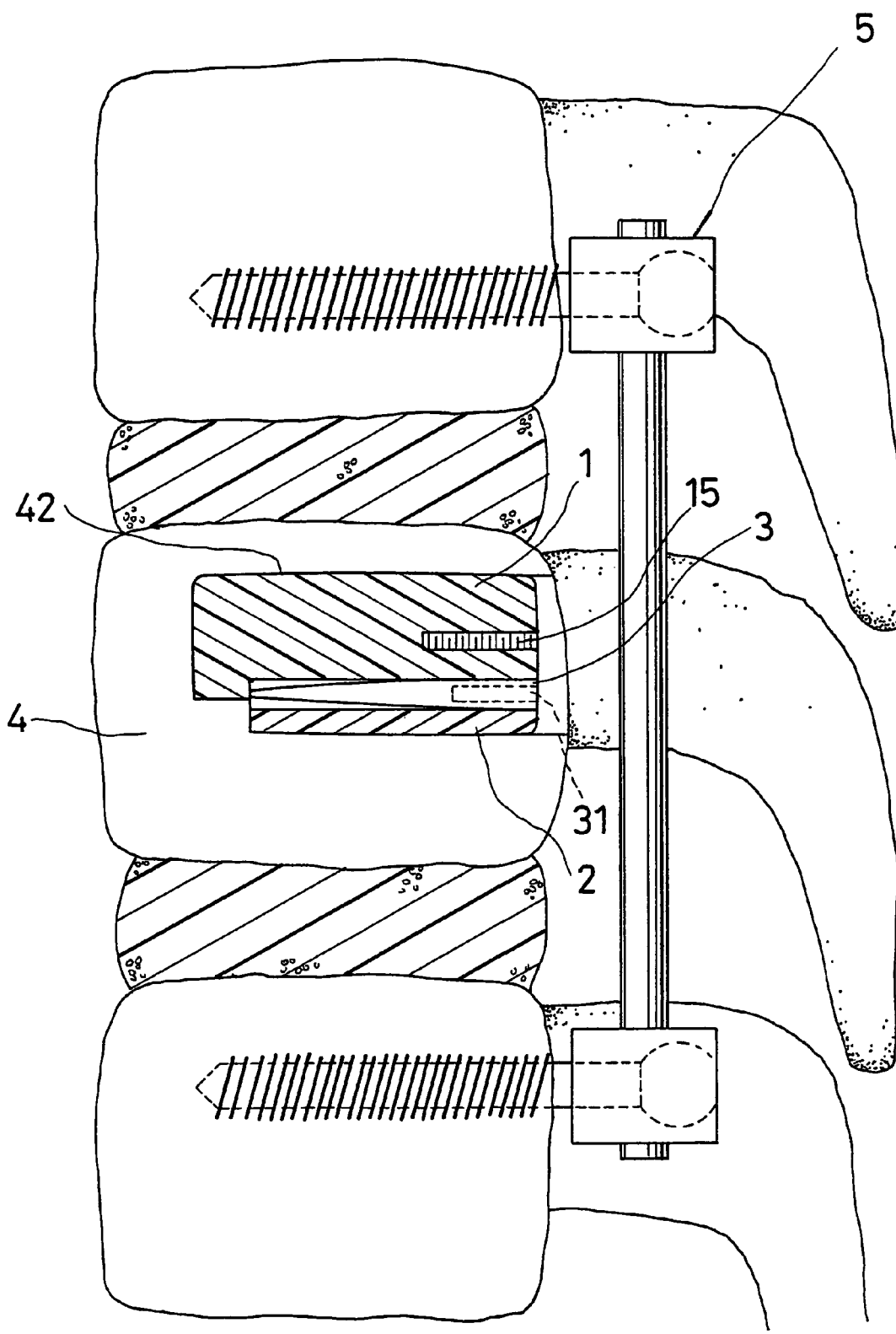
FIG. 3 is a view of the first embodiment of a distractable body augmenter for vertebral body reconstruction, used in another way.
Figure 4:
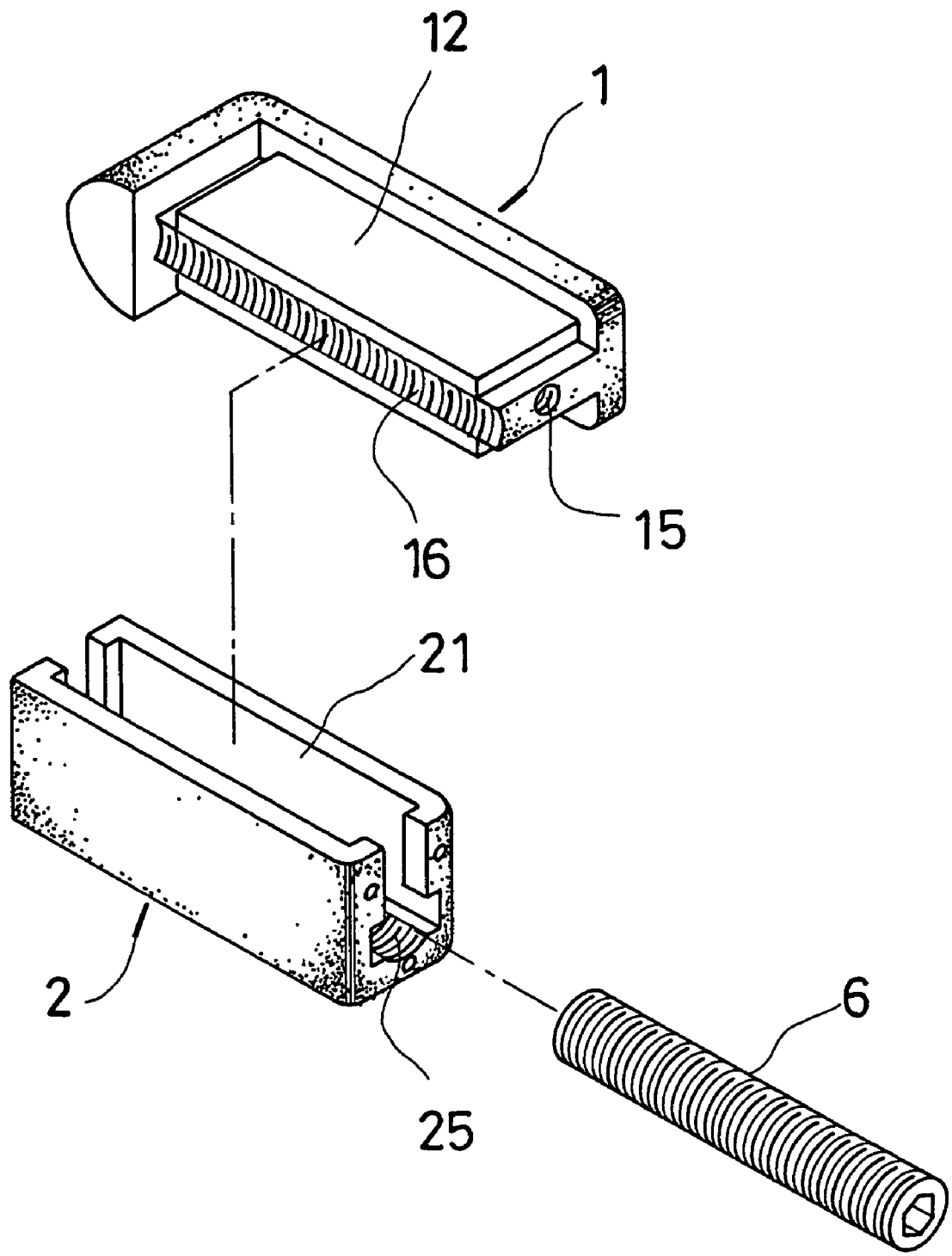
FIG. 4 is an exploded perspective view of the second embodiment of a distractable body augmenter for vertebral body reconstruction.

Referring to FIG. 3, if it is necessary, a screw system 5 can be applied to both of the vertebras next to the vertebra 4 for helping increase stability of the spine after planting of the distractable body augmenter of the present invention.

Figure 5:
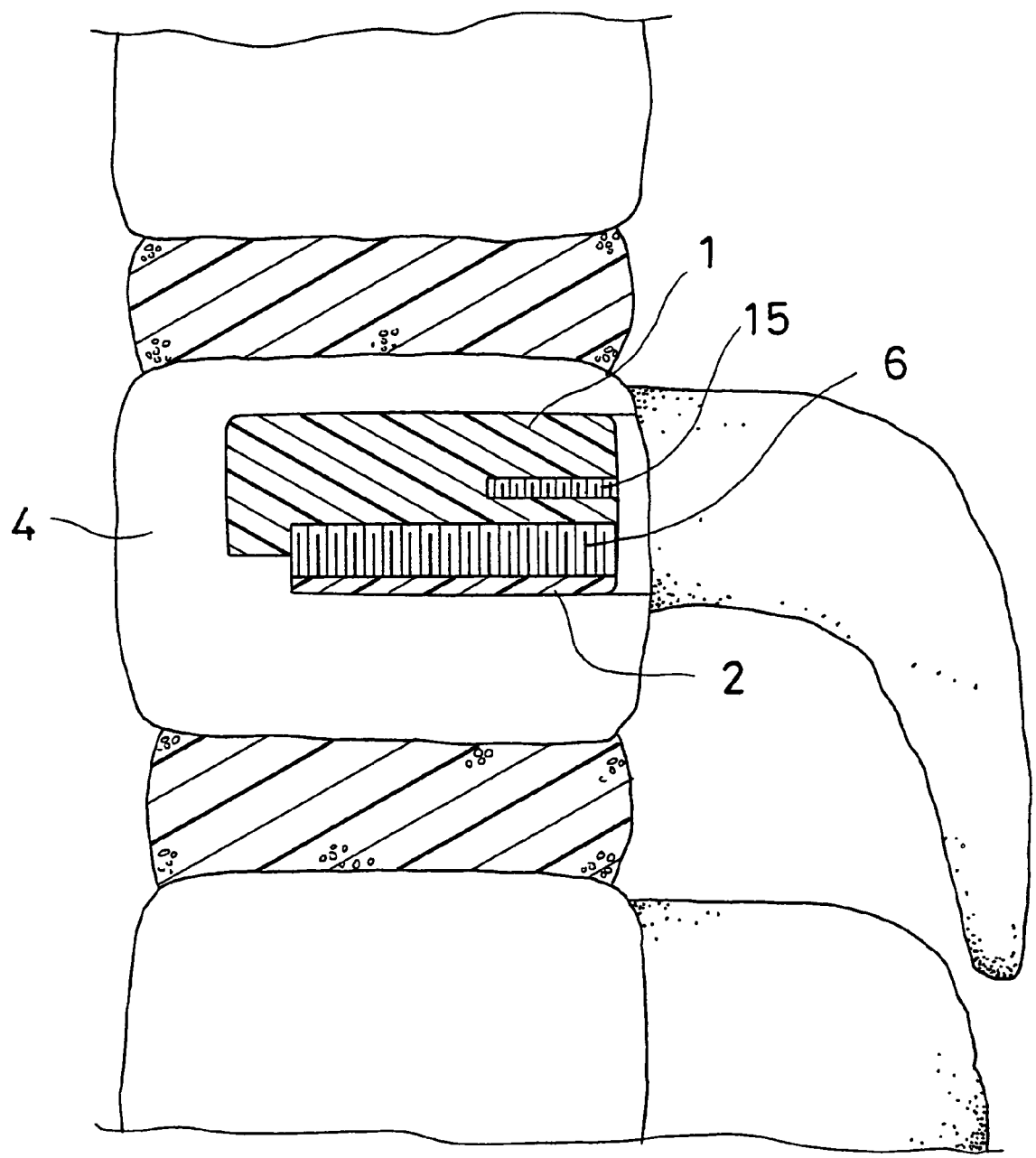
FIG. 5 is a view of the second embodiment of a distractable body augmenter for vertebral body reconstruction, planted in a vertebra.

The dimension of the distractable body augmenter is decided according to the vertical cross-section and the height of the pedicle 41 of the vertebra 4; the vertical cross-section of the pedicle 41 is close to a rectangle, and somewhat oval, and the distance from an upper end to a lower end of the pedicle 41 is larger than that from a rear end to a front end; the ratio of the height of pedicle 41 to the height of the vertebra 4 is between 0.5 and 0.6. Therefore, the augmenter can be made with a size near to the pedicle 41 so that at least 50% to 60% of the vertebra 4 is reconstructed. Consequently, 70% to 80% of the vertebra 4 will be reconstructed when the augmenter is combined with the rest of the vertebra 4. Furthermore, the height of the distractable body augmenter will be changed up to 30% by means of changing the thickness of the wedge-shaped bar 3, and in turns, the vertebra 4 can nearly recover the original size, which it had before the fracture. Therefore, with the help of second embodiment of an augmenter for vertebral body reconstruction, insertion portion 12 of upper planted block 1 is formed with a concavely curved side on a lower end thereof, and raised lines 16 spaced apart on the concavely curved side thereof while lower planted block 2 is formed with a concavely curved portion on an upper side of a bottom thereof, and raised lines 25 spaced apart on the concavely curved portion thereof. And, a screw element 6, which has threads, is screwed, with the help of the raised lines 16 and 25, into the space between the concavely curved side of the insertion portion 12 and the concavely curved portion of the lower planted block 2 to keep the planted blocks 1 and 2 in desired position relative to each other, as shown in FIG. 5.

Figure 6:
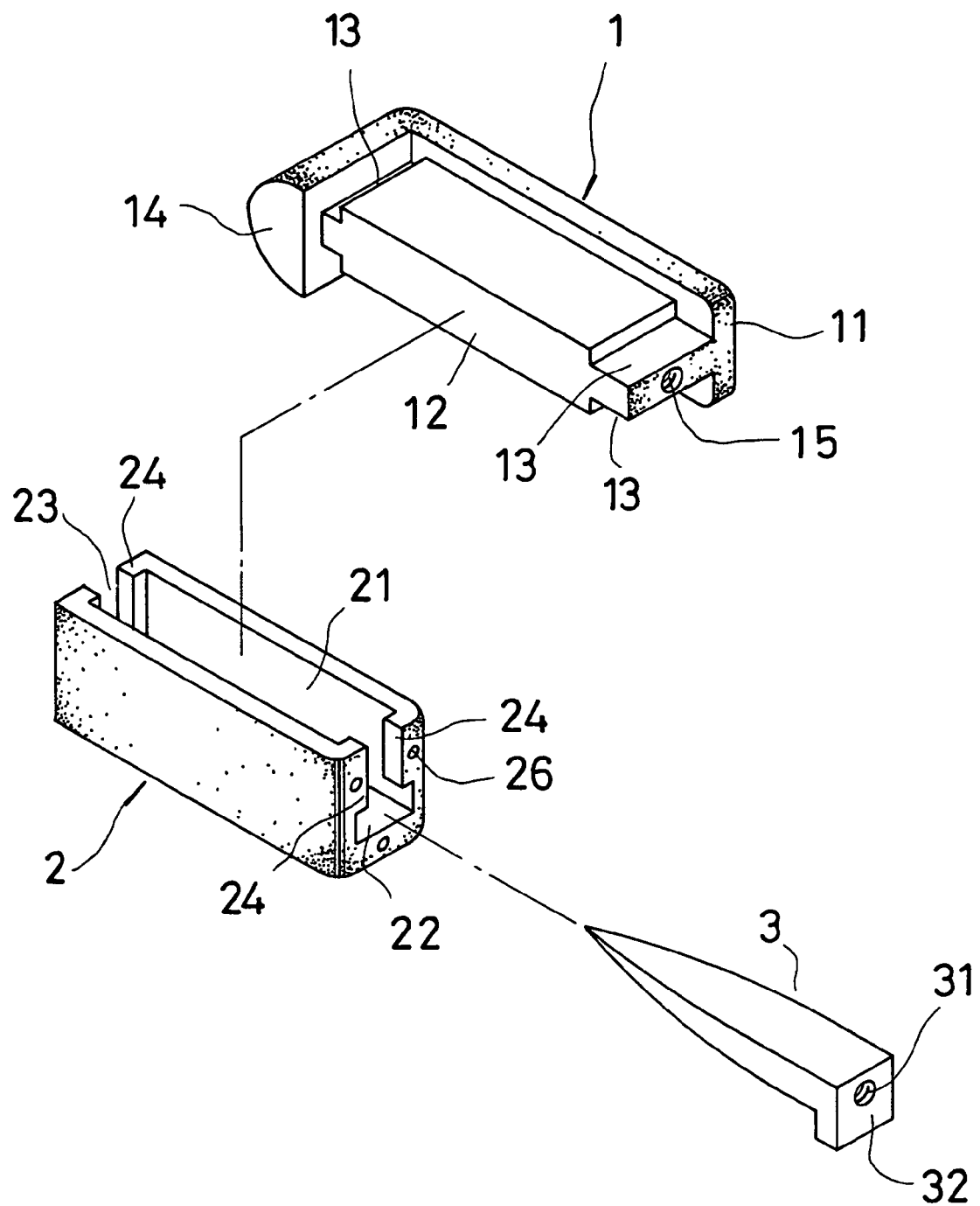
FIG. 6 is an exploded perspective view of the third embodiment of a distractable body augmenter for vertebral body reconstruction.
Figure 7:
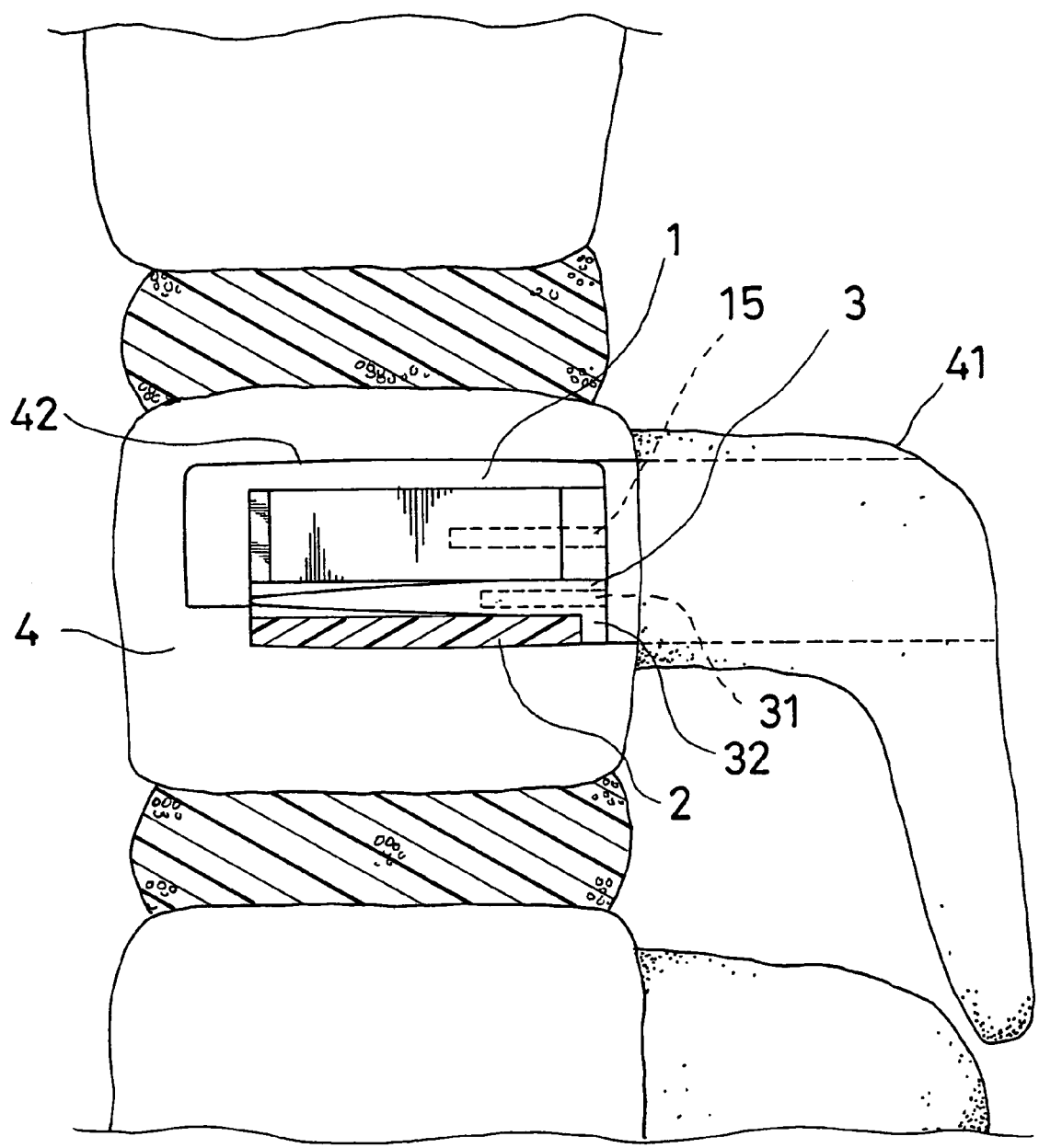
FIG. 7 is a view of the third embodiment of a distractable body augmenter for vertebral body reconstruction, planted in a vertebra.

Referring to FIG. 6, which is an exploded perspective view of the third embodiment of an augmenter for vertebral body reconstruction, wedge-shaped bar 3 is further formed with a downwards projecting extension portion 32 at a front end thereof while several holes 26 are formed on the front end of the lower insertion block 2. Thus, another tool can be connected with the holes 26 to help the augmenter planted in the vertebra 4, and the front ends of the upper and the lower planted blocks 1 and 2 will be co-planar in the vertebra 4, as shown in FIG. 7.

From the above description, it can be easily understood that the distractable body augmenter of the present invention has advantages as followings:

1. The distractable body augmenter is planted in a collapsed vertebra via the pedicle of a vertebra instead of via the thoracic or abdominal cavity of the patient therefore the operation is relatively safe, and mechanical strength of the vertebra is increased.
2. The distractable body augmenter can be used alone on a collapsed vertebra without the need for operation being done on other healthy vertebras near to the collapsed vertebra, which operation will cause the other healthy vertebras to lose the freedom to move.
3. Because the distractable body augmenter has a rough surface with small bumps all over, after the planting hole 42 is filled with harvested autogenous bone graft or artificial bone, the bone will be more firmly connected with the distractable body augmenter, and the connection of the bone sponge bone of the vertebra with the harvested autogenous bone graft (or artificial bone) will be more stable.
4. By means of inserting a wedge-shaped bar with suitable size in between the upper and the lower planted blocks 1 and 2, the distractable body augmenter will be enlarged to a suitable height for supporting the vertebra in a desired position.

What is claimed is:

1. A distractable body augmenter capable of being planted through a pedicle of a vertebra for vertebral body reconstruction, comprising:

an upper planted block, the upper planted block having an insertion portion projecting down from a lower side of an uppermost portion thereof and having a screw hole on a front end thereof;

a lower planted block fitted on the upper planted block, the lower planted block having a holding cavity between two lateral portions thereof, the upper planted block being fitted in the holding cavity at the insertion portion thereof; and a wedge-shaped bar having a screw hole on a front end thereof, the wedge-shaped bar being inserted between a lower end of the insertion portion and an upper side of a bottom of the lower planted block for causing longitudinal displacement of the upper and the lower planted blocks after the planted blocks together have been planted in a vertebra via a planting hole of a pedicle of the vertebra, wherein the insertion portion of the upper planted block has longitudinal fitting trenches on two sides of a front end and a rear end thereof while the lower planted block has an inverted T-shaped gap at a front end thereof, and an U-shaped gap at a rear end thereof, the front and the rear ends of the insertion portion being respectively fitted in the inverted T-shaped gap and the U-shaped gap of the lower planted block.

2. The distractable body augmenter as claimed in claim 1, wherein the upper planted block has a rough surface.

3. The distractable body augmenter as claimed in claim 1, wherein the lower planted block has a rough surface.

4. The distractable body augmenter as claimed in claim 1, wherein the lower planted block has a plurality of holes on the front end thereof for connection with a planting tool.

5. The distractable body augmenter as claimed in claim 1, wherein the wedge-shaped bar is further formed with an extension portion projecting downwards from the front end thereof.

6. A distractable body augmenter capable of being planted through a pedicle of a vertebra for vertebral body reconstruction, comprising:

an upper planted block, the upper planted block having an insertion portion projecting down from a lower side of an uppermost portion thereof and a screw hole on a front end thereof, the insertion portion having a concavely curved side on a lower end thereof and a plurality of spaced apart raised lines being formed on the concavely curved side of the insertion portion;

a lower planted block fitted on the upper planted block, the lower planted block having a holding cavity between two lateral portions thereof, the lower planted block having a concavely curved portion on an upper side of a bottom thereof, a plurality of spaced apart raised lines being formed on the concavely curved portion of the lower planted block, the upper planted block being fitted in the holding cavity at the insertion portion thereof; and a screw element formed with threads, the screw element being screwed into a space between the concavely curved side of the insertion portion and the concavely curved portion of the lower planted block after the planted blocks together have been planted in a vertebra via a planting hole of a pedicle of the vertebra, wherein the insertion portion of the upper planted block has longitudinal fitting trenches on two sides of a front end and a rear end thereof while the lower planted block at a front end has a plurality of holes for connection with a planting tool and an inverted T-shaped gap, and an U-shaped gap at a rear end thereof, the front and the rear ends of the insertion portion being respectively fitted in the inverted T-shaped gap and the U-shaped gap of the lower planted block.

7. The distractable body augmenter as claimed in claim 6, wherein the upper planted block has a rough surface.

8. The distractable body augmenter as claimed in claim 6, wherein the lower planted block has a rough surface.

* * * * *